United States Patent [19]

Bengmark et al.

[11] Patent Number: 5,152,770

[45] Date of Patent: Oct. 6, 1992

[54] IMPLANTABLE DEVICE FOR OCCLUDING A DUCT IN THE BODY OF A LIVING BEING

[75] Inventors: Stig Bengmark; Bo Persson, both of Lund, Sweden

[73] Assignees: AB Hepar; Surg Develop AB, both of Lund; AB Nolato, Torekov, all of Sweden

[21] Appl. No.: 673,818

[22] Filed: Mar. 22, 1991

[30] Foreign Application Priority Data

Mar. 22, 1990 [SE] Sweden .............................. 9001033

[51] Int. Cl.⁵ .............................................. A61B 17/12
[52] U.S. Cl. .................................. 606/157; 606/158; 606/202; 606/203; 128/DIG. 25
[58] Field of Search ............... 606/202, 203, 157, 158; 128/DIG. 25

[56] References Cited

U.S. PATENT DOCUMENTS

| | | | |
|---|---|---|---|
| 2,571,461 | 10/1951 | Livingston et al. | 606/202 |
| 4,399,809 | 8/1983 | Baro et al. | 128/1 |
| 4,428,365 | 1/1984 | Hakky | 128/DIG. 25 X |
| 4,531,519 | 7/1985 | Dunn et al. | 128/327 |
| 4,881,939 | 11/1989 | Newman | 128/DIG. 25 X |

FOREIGN PATENT DOCUMENTS

| | | |
|---|---|---|
| 3016522 | 11/1980 | Fed. Rep. of Germany . |
| 3715875 | 11/1987 | Fed. Rep. of Germany . |
| 695842 | 12/1930 | France . |
| WO8800454 | 1/1988 | PCT Int'l Appl. . |

Primary Examiner—Michael H. Thaler
Attorney, Agent, or Firm—Cushman, Darby & Cushman

[57] ABSTRACT

An implantable device for occluding a body duct, especially a blood vessel. The device includes a flexible, elongate plate to be fixed around the duct, a plurality of communicating bulbs which are arranged on one side of the plate and have a variable volume, and a connection for supplying fluid to the bulbs for occluding the duct and for evacuating fluid from the bulbs to open the duct after the occlusion. The flexible plate has a perforation at one end and a locking member in the form of a thickened portion at the other end. The locking member is passed through the perforation for safely fixing the device around the body duct.

To improve the occlusive function of the device, the bulbs may be made of an elastic material, the thickness of which is smallest at the tops of the bulbs.

6 Claims, 2 Drawing Sheets

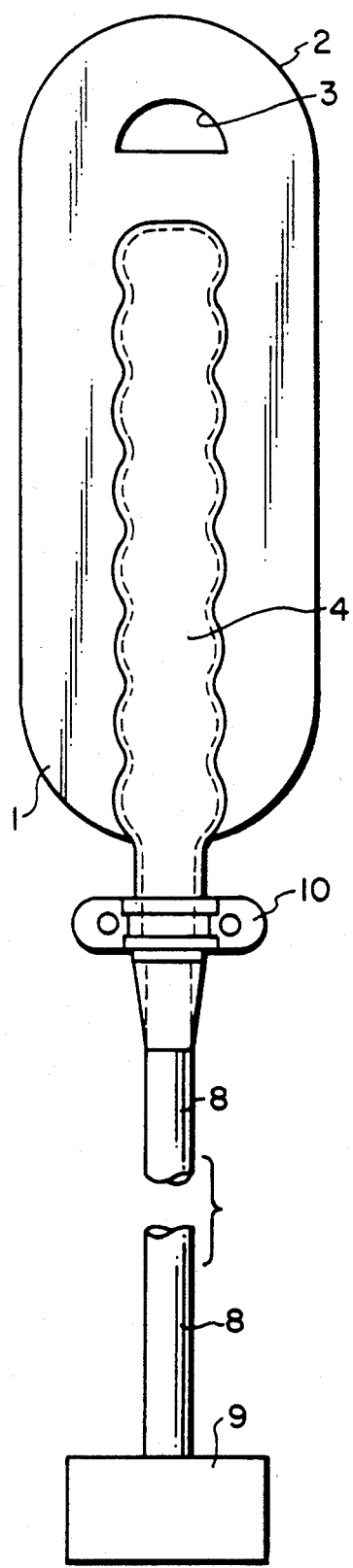
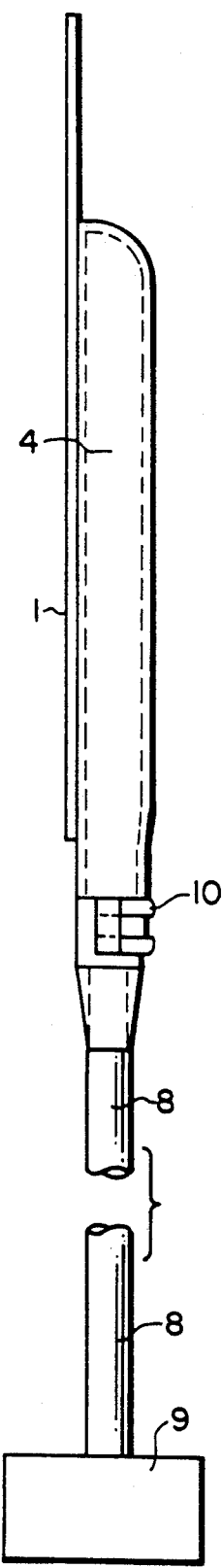
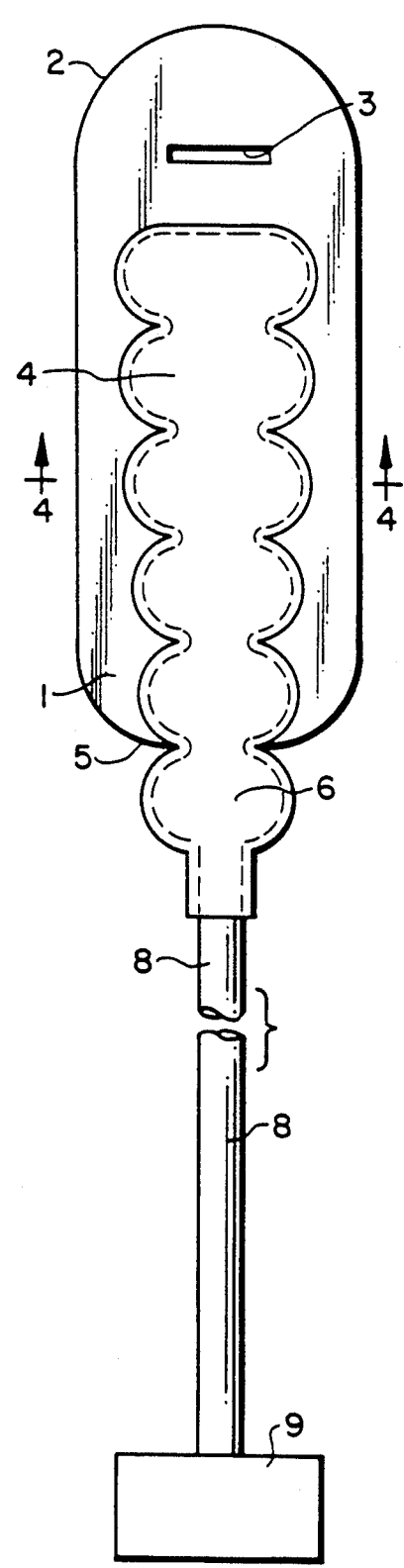
FIG. 1
FIG. 1a
FIG. 2

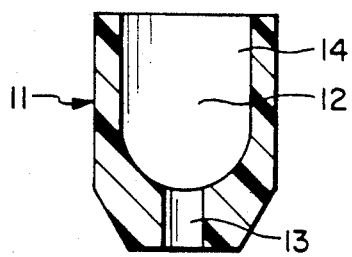
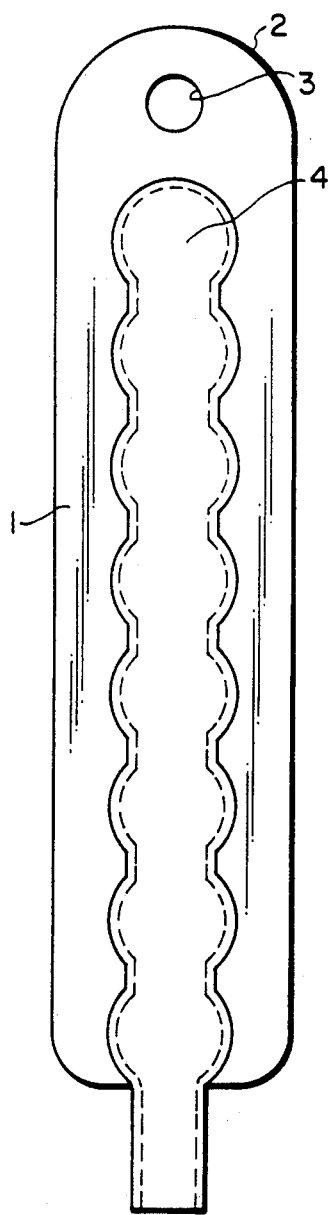
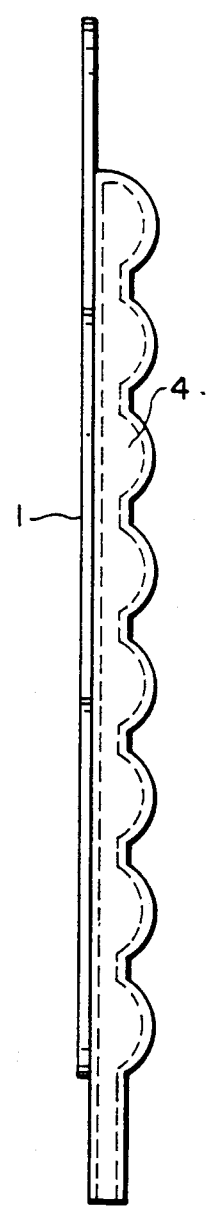

IMPLANTABLE DEVICE FOR OCCLUDING A DUCT IN THE BODY OF A LIVING BEING

BACKGROUND OF THE INVENTION

The present invention relates to an implantable device for occluding a duct, especially a blood vessel, in the body of a living being, which device is of the type comprising a flexible, elongate plate to be fixed around the duct, a plurality of communicating bulbs which are arranged on one side of the plate and have variable volume, and a connection for supplying fluid to the bulbs for occluding the duct and for evacuating fluid from the bulbs to open the duct after the occlusion.

A known approach for treating cancer of the liver is ischaemic treatment, in which the arterial blood flow to the tumor cells is occluded for limited periods of time. The publication "Repeated Liver Ischemia with an Implantable Vascular Occluder", Advances in Regional Cancer Therapy, III Int. Conf. Ulm 1987, pp 20-26 (Karger, Basel 1988) discloses a device for occluding the blood flow through a blood vessel. This device comprises a flexible, elongate strip or plate of silicone, on which a balloon is centered. In connection with a surgical operation, the plate is applied around the blood vessel to be occluded, and its ends are sewn together so as to provide a ring or cuff of suitable diameter around the blood vessel. The balloon is connected to a silicone catheter, in turn connected to a subcutaneous injection port with a self-sealing silicone membrane which permits repeated puncture and injection of fluid. In ischaemic treatment, the balloon is filled with fluid, thus increasing its volume and compressing the blood vessel, so as to obstruct the supply of blood. When the blood vessel is again to be opened, the fluid is sucked out of the balloon.

This prior art device suffers, however, from a number of drawbacks.

In particular, in some cases the blood flow is not completely occluded since the compression occurs only from one side of the blood vessel. In an improved device, the compression of the blood vessel should occur concentrically. Experiments have shown that if the device described above is modified such that the balloon extends around the entire blood vessel, creases are often formed, shutting off certain parts of the balloon and resulting in incomplete evacuation thereof. Moreover, high local pressures may arise, with a consequent risk of pressure-induced necroses.

Other drawbacks of the known device relate to the fixing of the plate around the blood vessel. For instance, it is difficult to attach the device in a manner which is neither too tight, nor too loose. If, on the one hand, it is attached too tightly, there is an obvious risk of permanent total occlusion. If, on the other hand, it is attached too loosely, the balloon may risk, when being inflated, to "roll out" on either of the sides of the plate, whereby the compression becomes insufficient. It is also difficult to adjust the known device to different blood vessel diameters.

Further, the balloon may risk to become damaged by the needle used for sewing together the plate ends. Repeated inflation of the balloon, which may occur a vast number of times, also leads to substantial strain on the sutures which may easily become loose or cut into the plate.

U.S. Pat. No. 4,399,809 discloses a device for providing a substantially concentric occlusion of a blood vessel. This device, which is an artificial sphincter, comprises a flexible strip having at least one row of inflatable chambers or bubbles extending in the longitudinal direction of the strip and communicating with each other. In use, the chambers are filled with and emptied of fluid through a hose passing from one of the chambers to a chamber in a manually-operated pump. This device does not solve the problems related to the fixing of an occlusion device around a duct.

DE-3,715,875 describes a device for occluding a body vessel, comprising a catheter provided with two spaced-apart bellows in fluid communication with the catheter. The catheter is to be placed in a loop around a body vessel, the fixing of the catheter being effected by means of a figure eight-shaped holder which is fixed to the catheter before the bellows and in which the free end of the catheter located on the other side of the bellows is inserted.

In this case, the occlusion of the body vessel is brought about by clamping the body vessel between the two planes defined by the bellows, whereby the walls of the body vessel are pressed out sideways.

SUMMARY OF THE INVENTION

One object of the present invention is to provide an improved device in which the above-related shortcomings of the known devices have been overcome and which, especially, can be attached around a body duct in a reliable and simple manner.

Another object of the invention is to provide a device for ensuring reliable and complete occlusion of the body duct with a reduced risk of pressure-induced necroses.

These objects are achieved by means of a device of the type described by way of introduction, in which the flexible plate has a perforation at one end thereof, and locking means in the form of a thickened portion at the other end thereof, the locking means being adapted to be passed through the perforation for fixing the device around the duct.

The plate has a perforation at one end and a locking means at the other end. In one embodiment, the locking means is a winged or butterfly-type flexible member provided on a connection for fluid supply/evacuation. In another embodiment, the locking means is a bulb, preferably the one located closest to the end remote from said perforation. For fixing the device around a duct, the locking means is passed through the perforation, thus ensuring safe locking.

In one embodiment, the device can be adjusted to different blood vessel diameters.

The bulbs, arranged in a row along the plate, preferably have the same width, but may alternatively have an increasing, or otherwise varying width towards the perforated end of the plate.

In one embodiment, the bulbs are made of an elastic material, whose thickness is smallest at the very tops of the bulbs. By this design, the bulbs will expand substantially in a direction normal to the plate when being filled with fluid. This, too, contributes to a more efficient occlusion.

The use of the device according to the present invention is of course not restricted to ischaemic cancer therapy. Other possible applications are:

a) As occluder around a newly-shaped orifice of the stomach in obese patients. By adjusting the size of this orifice, an ideal slimming rate can be obtained.

b) As occluder around blood flow by-passes in connection with e.g. liver cirrhosis surgery. By opening and closing the occluder, the by-passed amount of blood can be adjusted.

c) As occluder around the bladder neck or the urethra for treating incontinence.

BRIEF DESCRIPTION OF THE DRAWINGS

The invention will be described in more detail hereinbelow in one embodiment thereof with reference to the accompanying drawings, in which:

FIG. 1 is a top plan view of an occlusion device according to the invention, which is connected to a catheter and a control unit.

FIG. 1a is a side view of the occlusion device in FIG. 1.

FIG. 2 is a top plan view of a variant of the occlusion device in FIG. 1.

FIG. 3 is a cross-sectional view of a sleeve which can be used in the invention device.

FIG. 4 is a cross-sectional view of the device in FIG. 2 taken along the line 4—4 of FIG. 2.

FIG. 5 is a top plan view of a portion of another variant of the occlusion device in FIG. 1, and FIG. 5a is a side view of the portion of the occlusion device in FIG. 5.

DESCRIPTION OF THE PREFERRED EMBODIMENT

FIG. 1 shows an implantable device for occluding a body duct, especially a blood vessel. The device comprises an elongate strip or plate 1, one end 2 of which is rounded and provided with a perforation 3, which may be a slot or, as in FIG. 1, a crescent-shaped aperture.

On one side of the plate 1, a row of bulbs 4 is arranged in the longitudinal direction of the plate. The number of bulbs may vary, but preferably is in the range of 5–15. The bulbs 4 are arranged close to each other and also communicate with each other. The bulbs together form a substantially rectangular balloon where the difference between the maximum width of the bulbs and the width between two adjoining bulbs may vary. The advantage of having a smaller difference in width is that air can be more easily evacuated from the bulbs. As appears from the embodiment of FIG. 1a, the top surface of the balloon is even. In an alternative embodiment shown in FIGS. 5 and 5a, the balloon however has a different design, in which the bulbs do not merge into each other as completely as in the embodiments of FIGS. 1 and 1a.

At the end 5 of the device remote from the perforation 3, the bulbs are connected to a catheter 8, which may be detachable or integrally formed with the bulbs. The catheter 8 in turn is connected to a control unit 9, schematically illustrated as a box. The control unit 9 may comprise a known subcutaneous injection port which allows injecting and withdrawing fluid by means of a hypodermic syringe which is passed through the skin and into the injection port 9. Alternatively, the control unit 9 may comprise a motor-driven pump device, controlled e.g. by an ultrasound transceiver outside the body.

The catheter 8 has a locking means 10 in the form of a winged or butterfly-type flexible member.

When using the device, the plate is applied around the duct to be occluded, the catheter 8 is passed through the perforation 3, and the locking means 10 is forced through the perforation to ensure reliable fixing.

FIG. 2 shows a variant of the device in FIG. 1, with a different design of the locking means and the bulbs. In this case, the bulbs have an increasing width towards the perforated plate end 2. Further, the bulb located adjacent the plate end 5 remote from the perforation 3, i.e. the smallest bulb 6 in FIG. 2, is used as locking means. As shown in this Figure, the bulb 6 is located outside the plate end 5, such that it can be passed through the perforation 3 together with the catheter 8. When the bulbs are thereafter filled with fluid, the smallest bulb 6 cannot be retracted through the perforation 3, whereby safe locking is achieved.

Alternatively, the plate 1 may be formed with two slots which extend inwards from the respective long sides of the plate 1 towards the bulbs in the area between the smallest and the second smallest bulb and which enable the smallest bulb and the corresponding plate portion to be passed through the perforation.

It is also conceivable to use more than one bulb as locking means, i.e. to lock the device around a blood vessel by passing, e.g., the two smallest bulbs through the perforation 3. In this case, both bulbs must be separated from the plate, or protrude outside the plate end 5, or the plate must be provided with slots or otherwise arranged to permit passing the bulbs through the perforation.

In the case where one or more bulbs are used as locking means, it may be suitable to make this one bulb or these bulbs exceptionally strong by making the bulb wall thicker than in the other bulbs and/or by surrounding said bulb or bulbs with a sleeve to obviate the risk of crack formation.

FIG. 3 is a cross-section of a sleeve 11 which can be used for strengthening the bulb 6 in FIG. 2. The sleeve has a channel 12, one end of which has a smaller-diameter portion 13 and the other end of which has a larger-diameter portion 14. When the smallest bulb 6 has been passed through the perforation 3, the sleeve is suitably placed on the catheter and forced onto the bulb 6, thus reinforcing the walls thereof. When the sleeve is in place, the bulb 6 is thus located in the sleeve portion 14, while the part of the catheter 8 closest to the bulb 6 is located in the sleeve portion 13.

FIG. 4 is a cross-section of the device shown in FIG. 1. From this figure, it appears that the thickness of the bulb wall decreases towards the top or apex of the bulb. When the bulb is filled with fluid, it will thus expand substantially in a direction normal to the plate 1. Advantageously, at least some of the bulbs are of this design.

The device is preferably made of rubber or plastic, e.g. silicone rubber or polyurethane. The plate 1 is optionally coated with titanium to minimise tissue reaction.

What we claim and desire to secure by letters patent is:

1. An implantable device for occluding a duct in the body of a living being, by circumferentially surrounding and radially inwardly compressing the duct,
said device comprising:
a flexible plate elongated along a longitudinal axis and having two opposite faces, two opposite longitudinal edges, and two opposite transverse ends;
a longitudinally elongated elastic bulb member comprising a succession of serially interconnected bulbs which relatively expand in volume upon inflation and contract in volume upon deflation, said bulb member having two opposite ends;

a port means communicating with one end of said bulb member for inflating said bulbs and for permitting said bulbs to deflate;

said bulb member being mounted on one face of said plate;

means defining at least one opening through said plate from one to the other of said faces, adjacent one said end of said plate, each said opening having a first given width;

said bulb member having an opposite end from said one end thereof disposed adjacent said at least one opening through said plate;

a locking means associated with said bulb member and located adjacent said one end of said bulb member axially beyond where said bulb member is mounted on said one face of said plate, said locking means having a second given width which is broader than said first given width, but being flexible, so that said device can be coiled about an axis which is transverse to said longitudinal axis, so as to juxtapose said ends of said plate with said bulb member surrounding a duct which is to be occluded, and said locking means can be elastically manipulated to force it through said opening, so that said locking means engages against an opposite said face of said plate.

2. The device of claim 1, wherein:
said locking means comprises a winged flexible member provided on said port means axially beyond said opposite end of said plate.

3. The device of claim 1, wherein:
said bulbs decrease in width lengthwise of said bulb member away from said at least one opening, terminating in at least one bulb of smallest width, and said at least one bulb of smallest width constitutes said locking means.

4. The device of claim 1, further comprising:
a catheter having one end effectively connected with said port means for inflating said bulbs and permitting said bulbs to deflate.

5. The device of claim 1, wherein:
each said bulb has a wall which arches from said one face of said plate, said wall varying in thickness by being thickest nearest said plate, and being thinnest centrally thereof, furthest from said plate.

6. The device of claim 1, wherein:
said plate, from end to end thereof is broader than said bulb member.

* * * * *